United States Patent
Cramer et al.

[19]

[11] Patent Number: 6,015,291
[45] Date of Patent: Jan. 18, 2000

[54] DENTAL ARTICULATOR

[75] Inventors: Rudolf Cramer, Sachsenkam, Germany; Rudolf Slavicek, Wien, Austria

[73] Assignees: Synthese Dentale Forschungs-und Entwicklungsgesellschaft mbH; Gamma Wisenschaftliche Fortbildungsgesellschaft mbh, both of Klosterneuburg, Austria

[21] Appl. No.: 09/104,624

[22] Filed: Jun. 25, 1998

[30] Foreign Application Priority Data

Jun. 26, 1997 [DE] Germany .......................... 197 26 978
Aug. 29, 1997 [DE] Germany .......................... 197 37 661

[51] Int. Cl.⁷ .................................................. A61C 11/02
[52] U.S. Cl. .............................................. 433/57; 433/54
[58] Field of Search .................... 433/54, 55, 57, 433/58, 60, 61, 66

[56] References Cited

U.S. PATENT DOCUMENTS

| | | | |
|---|---|---|---|
| 4,365,955 | 12/1982 | Tradowsky | 433/54 |
| 4,886,453 | 12/1989 | Ludwigs | 433/54 |
| 4,981,437 | 1/1991 | Wilcox . | |
| 5,057,014 | 10/1991 | Zeiser | 433/54 |
| 5,190,455 | 3/1993 | Schreiber | 433/54 |
| 5,281,135 | 1/1994 | Schwestka-Polly | 433/54 |
| 5,334,017 | 8/1994 | Lang et al. | 433/57 |
| 5,431,564 | 7/1995 | Guichet | 433/55 |
| 5,707,233 | 1/1998 | Hobo et al. | 433/55 |
| 5,807,102 | 9/1998 | Lang et al. | 433/64 |

FOREIGN PATENT DOCUMENTS 36 08 422 C2 12/1986 Germany .
42 11 020 C2 10/1993 Germany .

*Primary Examiner*—Ralph A. Lewis
*Attorney, Agent, or Firm*—Brooks & Kushman P.C.

[57] ABSTRACT

A dental articulator is disclosed, with condylar housings located in interchangeable fashion in mounts on the upper member of the dental articulator for accommodating and guiding condyles fixed to the lower member, where horizontal guide elements for the condyles for simulating the sagittal movements of the mandibular joint and Bennett guide elements for simulating the transverse movements of the mandibular joint are located in the condylar housing.

23 Claims, 9 Drawing Sheets

DENTAL ARTICULATOR

TECHNICAL FIELD

The invention relates to dental articulators housings located in interchangeable fashion in mounts on the upper member of the dental articulator for accommodating and guiding condyles fixed to the lower member, where horizontal guide elements for the condyles for simulating the sagittal movements of the mandibular joint and Bennett guide elements for simulating the transverse movements of the mandibular joint are located in the condylar housing.

BACKGROUND ART

Dental articulators for simulating mandibular joint movements usually consists of a lower member for accommodating a cast of the mandible or maxilla, generally made of plaster, and an upper member for accommodating the corresponding other cast. The lower member and upper member are provided with magnetic holders or other mounts.

In this context, the connection between the upper and lower members is made by condylar joints, which permit movement corresponding to the human mandibular joint. For this purpose, the rear end of the lower member is provided with two vertically arranged posts some distance apart, on which condylar balls are located, these engaging variable-angle condylar housings with corresponding guide elements from below. Depending on the design, it is, of course, also possible to locate the condylar housing on the posts and, accordingly, the condylar balls on the upper member, as described in U.S. Pat. No. 4,981,437, for example.

Furthermore, the front area of the lower member is provided with an incisal pin, on which the upper member rests via an incisal guide table. The incisal pin is used for anterior guidance when simulating the protrusion, retrusion and laterotrusion movements. Posterior guidance when simulating the transverse and sagittal movements on the mandibular joint side is provided by the guide elements, which are provided with sagittal condylar guides and transverse Bennett guides.

In order to be able to simulate these movements, the condylar balls are capable of movement in the three translatory and rotatory degrees of freedom within the condylar housings, or the condylar housings about the condylar balls. In addition, the angles of the condylar housings can also be varied.

The disadvantage of these dental articulators is the complicated structure of the condylar housings and the need to use a host of different guide elements, occasionally with three-dimensional guides or guides with complex curvatures, in order to reflect the natural situation. This results in the additional difficulty that the joint mechanism of the dental articulator first has to be adjusted prior to use. This is usually done by adjusting the position in space of the condylar ball in relation to the joint axis running through the condylar joint. Owing to the curvature of the sagittal condylar guide and the Bennett guide, it is impossible to achieve statically determined allocation of the condylar ball within the condylar joint. For this reason, the Bennett guides have to be replaced by straight guides for adjusting. These adjusting guides enclose an angle in relation to each other, at which the condylar ball is pressed and retained during adjustment.

Another disadvantage of this prior art is that the condylar housing sitting on the condylar ball is only accessible from below. Consequently, the upper member of the dental articulator has to be removed in order to change inserts. Moreover, the movement of the condylar ball in the condylar housing cannot be observed.

However, for purposes of functional diagnostics, another movement is of interest, which can only be reproduced incompletely, if at all, in articulators of the familiar design.

When a patient closes his lower jaw about the terminal hinged axis, it is often the case that, when contact is made, only one antagonistic contact occurs on only one antagonistic pair of teeth. As the jaw is closed further, the lower jaw is subjected to the automatic influence of the teeth and slides into a position with the best possible, stable tooth contact. This is the intercuspital position. The mandibular joints are dislocated accordingly in this context.

The direction and the extent of this three-dimensional displacement of the mandibular joints under the influence of the teeth are of importance.

As the condylar housings of conventionally designed articulators prevent movement of the condyles in an upward, rearward and possibly a lateral direction, these articulators do not permit the simulation and measurement of this position. For this purpose, plaster casts are therefore commonly transferred to special "joint position measuring instruments", the design of which is similar to that of articulators, but which are not restricted by condylar mechanisms. The condylar housings are replaced by corresponding measuring devices in this case.

DISCLOSURE OF INVENTION

For these reasons, the invention is based on the task of creating a dental articulator which, while offering good control, can be operated under forced control in all directions, which displays easily interchangeable and simple component parts and which also permits direct recording of the displacement of the mandibular joint in the intercuspital position.

According to the invention, the task is solved in a dental articulator of the type mentioned at the start in that, for spatially controlled guidance on the laterotrusion side, the condyle is designed as a condylar pin which extends in the joint axis through the condylar guide in the condylar housing connected to the upper member of the articulator in detachable fashion into the condylar housing and in that the free end of the condylar pin can be positioned against a guide surface of the Bennett guide element in the condylar housing.

This creates a dental articulator with a condylar housing which is inexpensive to manufacture and in which the Bennett guide and the condylar guide are spatially separated and can be replaced easily and independently of each other. In particular, this creates a condylar joint which is force-guided in all directions by different inserts, meaning that spatially controlled guidance on the laterotrusion side is possible in the sense of laterotrusion, laterosurtrusion, lateroretrusion, laterodetrusion and lateroprotrusion. Moreover, this offers the possibility for the first time of providing the upper side of the condylar housing with a viewport so that all the movements of the condylar pins in the condylar housing can be readily observed.

As a result of the vertical support of the condylar housing provided by the condylar insert, the condylar housing can be left open on one side in the direction of the upper side of the dental articulator, this making it possible to observe the movements in the condylar housing.

Another configuration of the invention is characterised in that the condylar housing is provided with an arc-shaped locating surface opposite the condylar insert to accommodate and allow limited swivelling of a mount with a semicircular cross-section for the Bennett insert. This mount can be fixed in position at a given angle on the locating surface.

Fixing of the mount is achieved in simple fashion in that the mount is provided with a locking screw which reaches through an arc-shaped slit in the base surface of the condylar housing, allowing the mount to be fixed on the base surface of the condylar housing by means of the locking screw.

In a further configuration of the invention, the mount is provided with a guide, into which the Bennett insert can be inserted in positive and slightly non-positive fashion through the opening in the condylar housing. The Bennett insert which can be inserted in this way offers the additional possibility of permitting individual guidance of the return swivelling movement of the condylar pin in the event of asymmetrical movement. This possibility is restricted in the known articulators. As a result, the condylar housing becomes fully adjustable in three dimensions, including on the working side of the articulator.

The slightly non-positive fastening of the Bennett insert is achieved in a simple manner by the one side of the guide being provided with a recess and a small gap being left free between the guide surface and the outer surface of the mount opposite the recess up to the end of the outer surface of the mount. This permits resilient deflection of this part of the mount to a small extent.

Moreover, the condylar insert is fastened in the condylar housing in replaceable fashion, where one end of its guide slit is open in the direction of the lower member of the dental articulator, so that the condylar housing can easily be placed onto the condylar pin.

The width of the guide slit should roughly correspond to the diameter of the condylar pin, so as to achieve guidance without play.

In a further configuration of the invention, the condylar insert can be fastened in the condylar housing positively and non-positively and/or in locking fashion. This ensures a secure fit in the condylar housing, on the one hand, and enables the condylar insert to be replaced without using tools, on the other hand. Furthermore, at least the side of the guide slit lying on the condylar pin when the dental articulator is in working condition is designed in accordance with natural condylar guidance.

The condylar insert has a geometrically simple contour and can be manufactured inexpensively from a suitable plastic, into which the corresponding slit can subsequently be milled with the required pathway form. Naturally, complete condylar inserts with standard shapes can also be manufactured by injection moulding, for example.

The condylar inserts can be designed in such a way that they permit rearward movement beyond the centre position on the laterotrusion side.

The angle of the condylar housing is preferably adjustable about the joint axis, where the position of the condylar joint can be easily adjusted to the natural inclination of the condylar plane of the mandibular joint.

A special configuration of the invention is characterised in that each side of the upper member of the dental articulator is provided with a condylar housing mounted in detachable fashion, where a condylar pin projecting inwards from the vertical post of the dental articulator protrudes into each condylar housing.

In a special configuration of the invention, the degrees of freedom of the condylar pin in the condylar housing can be restricted, so as to permit the prevention of undesirable movements.

For this reason, the condylar housing is provided with an articulated hook which can be swung onto the condylar pin in front of the condylar guide and which fixes the condylar joint in the centric position on the condylar pin. This means that the upper member of the dental articulator can then only be pivoted relative to the lower member, this facilitating the insertion of the plaster casts, for example, and also permitting simple control of the occlusal overlay in the centric position. Moreover, this also ensures safe transport of the dental articulator.

Advantageously, the hook can be positioned on the condylar pin in locking fashion, thus preventing its unintentional release.

To provide lateral blocking of the condylar function, the condylar pin additionally has an axially movable spacer ring, which can be fixed on the condylar housing, so that transverse movements can be inhibited.

The same effect is achieved by locating an additional post between the vertical posts on the lower member, the upper end of which is provided with an adjustable centric guide into which a locking pin mounted on the upper member can be inserted, so that only protrusion and retrusion movements are then possible.

The task on which the invention is based is moreover solved in that the upper member and lower member are fixed in space in relation to each other, that a measuring cube movable along the hinge axis is inserted in each mount, that each measuring cube is provided with an anti-twist device and displays a measuring surface opposite the associated condyles which is used for affixing a label for indicating the up/down and backward/forward offset, and that the measuring surface with the affixed label can be pressed against the condyle at a contact point.

This makes it simple to determine the displacement of the hinged axis in the intercuspital position relative to the zero reference position of the articulator in that the position of the upper member is fixed in space relative to the lower member by the plaster cast of the lower and upper jaw being inserted first. The plaster models of the lower and upper jaw must be brought together in the position of maximum intercuspitation in this context. Once the position reached has been recorded, the test and adjusting key is then inserted and the recording repeated in the zero reference position.

In a further configuration of the invention, the measuring surface is provided with a positioning edge for the label (graph paper), so that the label can easily be aligned in relation to the measuring surface.

In order to ensure exact recording of the position of the condyle in relation to the measuring surface, the measuring cubes with the measuring surfaces can be moved against the condyles after inserting a marking film, the measuring cubes permitting movement independently of each other.

In order to allow particularly simple and reliable mounting of the measuring cube, it is provided with a stud for inserting into the mount of the upper member and additionally possesses a tab which extends inwards in the axial direction and makes flat contact on the rear surface of the upper member when mounted. The tab thus serves to prevent twisting.

In a further configuration of the invention, the rear surface of the upper member is provided with a recording medium below the tab for recording the transverse offset with a marker pen. The inner edge of the tab can serve as a straightedge for this purpose. In this way, a mark indicating the transverse position of the hinged axis in space can be made on the recording medium.

Finally, it is of advantage if the free end of the condylar pin is rounded in the manner of a spherical cap. The free end of the condylar pin can also end in a ball or an undercut ball or spherical cap.

The invention is described in more detail below on the basis of a practical example.

BEST MODE FOR CARRYING OUT THE INVENTION

Figure 1:
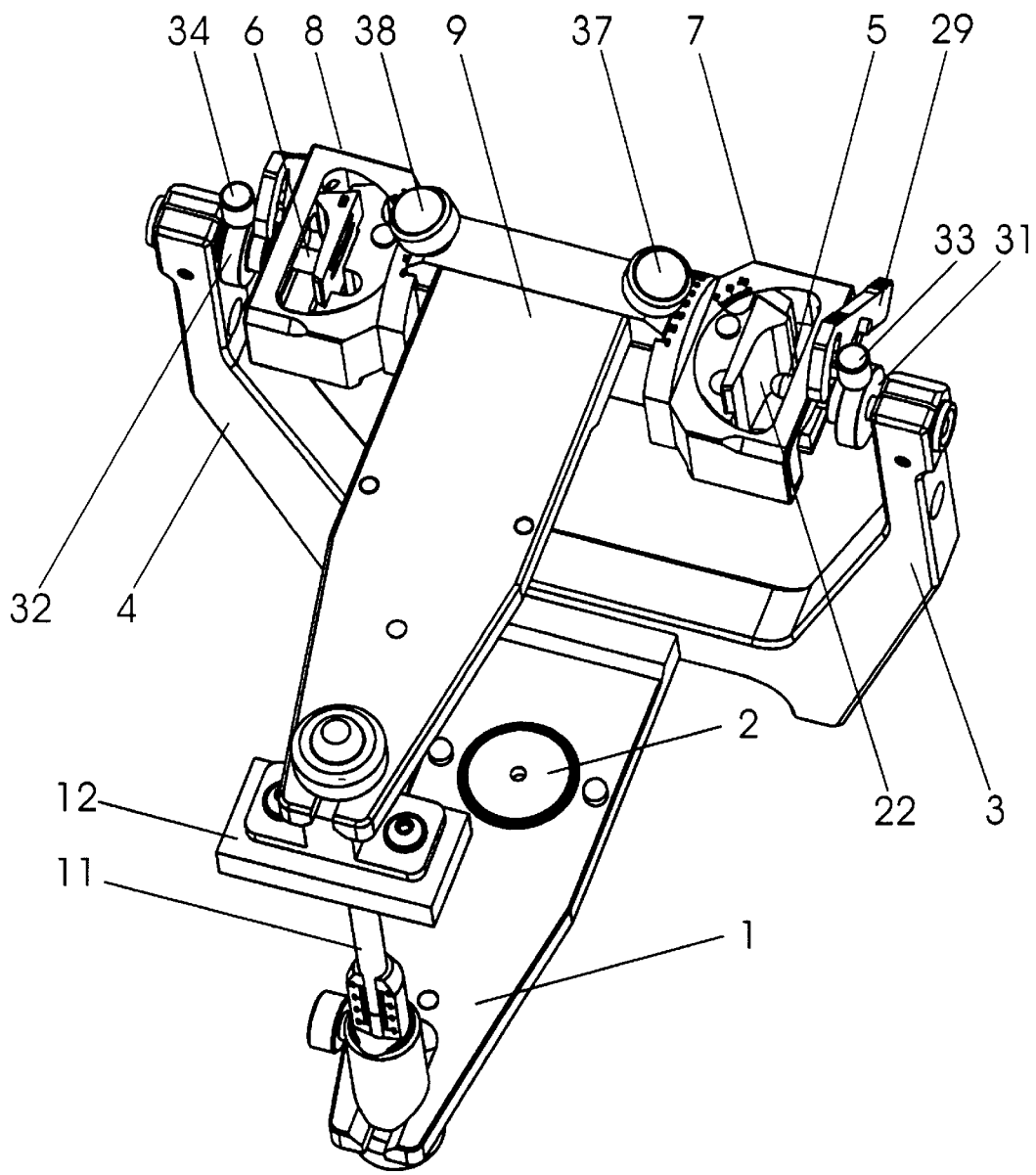
FIG. 1 a perspective top view of a dental articulator with the condylar joints according to the invention, FIG. 2 a bottom view of the upper member of the dental articulator as per FIG. 1, FIG. 3 a condylar housing according to the invention, FIG. 4 the condylar housing with different inserts, FIG. 5 a rear view of the dental articulator as per FIG. 1 with additional quick-action centric position lock, FIG. 6 the top view of the vertical post of the dental articulator as per FIG. 5 with quick-action centric position lock with removed upper member, FIG. 7 the measuring elements, inserted in the axial bores of the upper member of the articulator in place of the condylar housings, in order to determine the condyle positions, and displaying a measuring cube on either side, FIG. 8 an articulator with measuring cubes inserted in the upper member and a test and adjusting key for marking the zero reference point (RP), FIG. 9 a rear view of an articulator with measuring cubes inserted in the upper member and casts in the intercuspital position for measuring the transverse offset, and FIG. 10 the measuring elements as per FIG. 1 in a different presentation.
Figure 2:
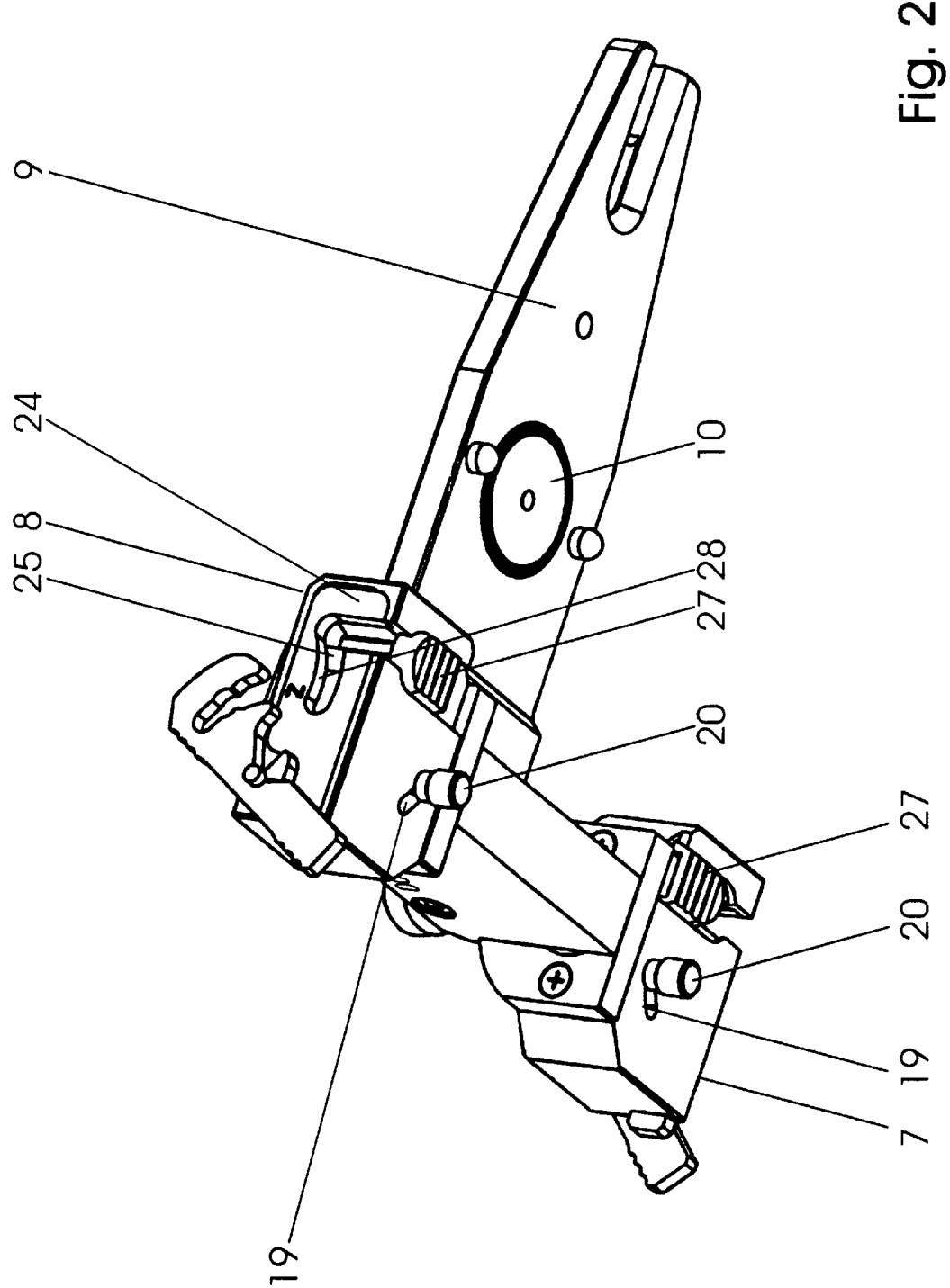

The dental articulator shown in the general view in FIG. 1 consists of a fixed lower member 1, which is provided with a mount 2 for a plaster cast of an upper or lower jaw (not shown). Two vertical posts 3, 4, arranged a certain distance apart, project from the rear area of lower member 1, the upper ends of which are provided with inward-pointing condylar pins 5, 6 and on each of which a condylar housing 7, 8 rests. These condylar housings 7, 8 are located on an upper member 9 of the dental articulator, which is likewise provided with a mount 10 for accommodating a further plaster cast of the corresponding other jaw (FIG. 2).

On the front area of the lower member, there is additionally a longitudinally adjustable incisal pin 11, which rests on an incisal guide table 12 on upper member 9. Incisal pin 11 is used to provide anterior guidance during protrusion, retrusion and laterotrusion movements.

As described below, posterior guidance during simulation of the transverse and sagittal movements of the mandibular joint side is provided with the aid of the condylar joint according to the invention by way of corresponding guide elements for condylar pins 5, 6 within condylar housing 7, 8.

Figure 3:
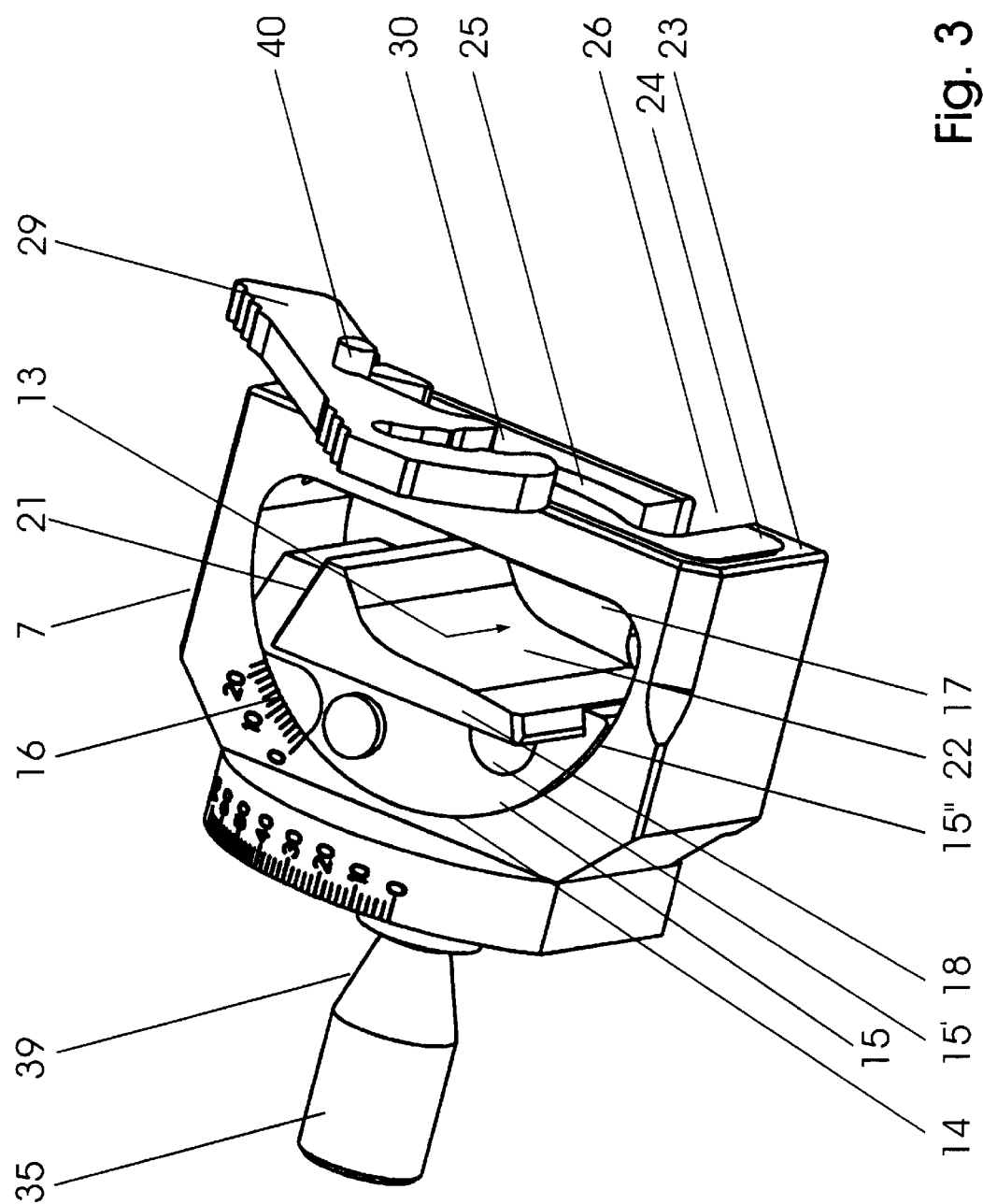
Figure 4:
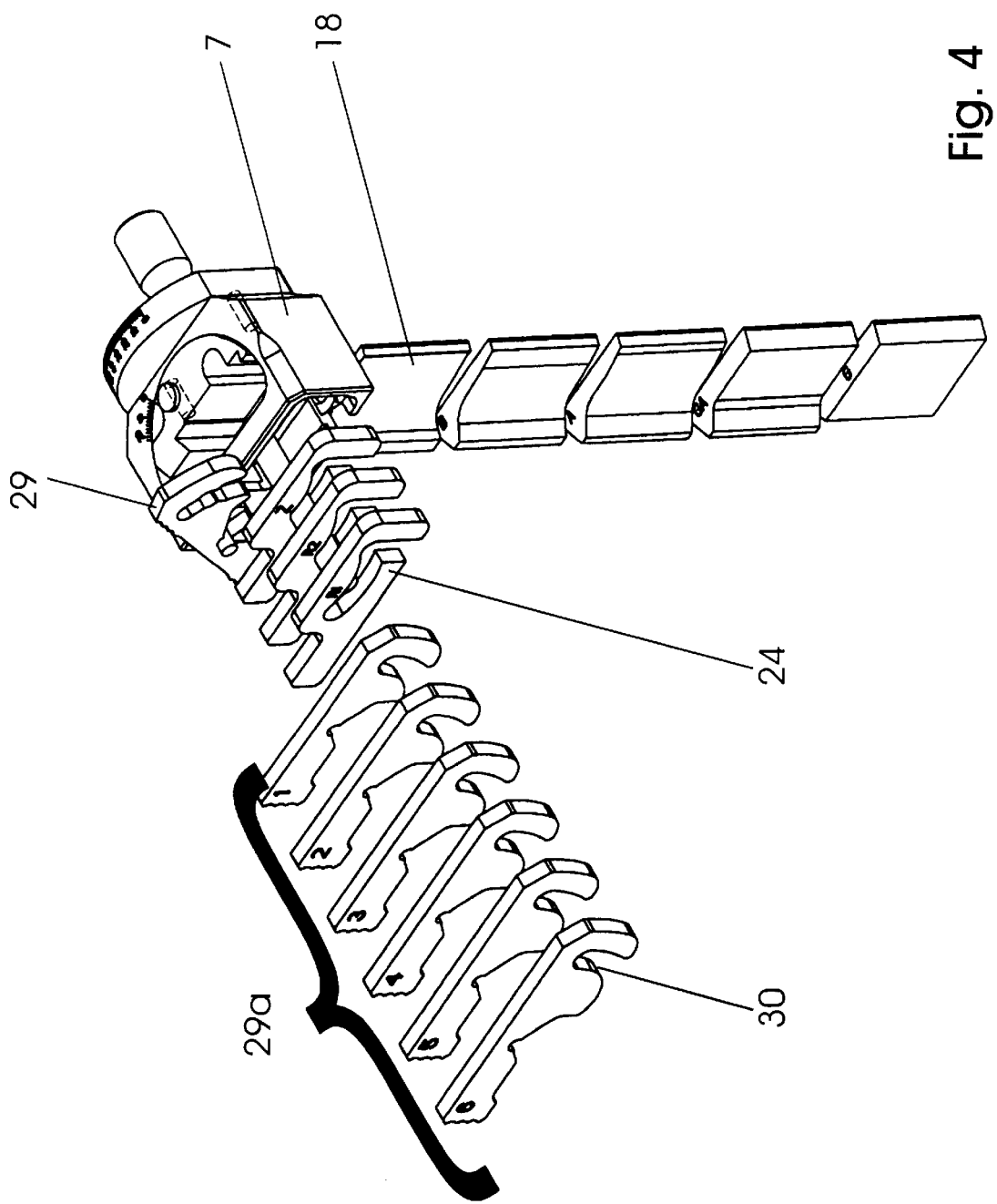

The special structure of the condylar housing 7, 8 can best be seen in FIGS. 3 and 4.

The interior of the condylar housing 7, 8 is freely accessible via an opening 13 located on its upper side and displays an arc-shaped locating surface 14 on one side to accommodate a mount 15 for interchangeable Bennett inserts 18. Mount 15 is guided on base surface 17 of condylar housing 7, 8, on the one hand, and with the aid of a forced guidance device on locating surface 14, on the other hand. This forced guidance device consists of an arc-shaped slit 19 in base surface 17, through which a locking screw 20 connected to the mount reaches. In this simple way, angular adjustment of mount 15 for Bennett insert 18 is ensured to the necessary extent in combination with a corresponding graduated scale 16.

To permit interchangeable accommodation of Bennett inserts 18, mount 15 is provided with a guide 21, into which Bennett inserts 18 can be inserted through opening 13. To this end, guide 21 is of dovetail design, for example. This makes it possible to insert Bennett inserts 18 into mount 15 in a positive and slightly non-positive fashion. Slightly non-positive accommodation of Bennett inserts 18 in mount 15 is achieved by one side of guide 21 being provided with a recess 15' and a small gap 15" being left free between guide surface 14 and the outer surface of mount 15 opposite recess 15' from this point up to its end. This gap 15" makes it possible for Bennett insert 18 to be slightly oversized in relation to guide 21, thus obtaining non-positive mounting when inserted in guide 21, as mount 15 is resilient and can give. If the fit is sufficiently accurate, further securing of Bennett inserts 18 is unnecessary, as their freedom of movement in the downward direction is limited by base surface 17 anyway.

Bennett insert 18 furthermore possesses a guide surface 22, against which the free end of condylar pin 5, 6 can be positioned. The free ends of condylar pins 5, 6 should be designed in the form of a spherical cap, or at least crowned, so that defined contact with Bennett insert 18 is guaranteed at all times. The same effect can be achieved if condylar pins 5, 6 each end in a ball, an undercut ball or spherical cap, or the like. In principle, the free end of condylar pins 5, 6 can also be provided with a point, although this would cause appreciable wear on guide surface 22 of Bennett insert 18.

In order to realise vertical guidance of condylar pin 5, 6 in condylar housing 7, 8, face end 23 of the latter opposite locating surface 14 is fitted with a condylar insert 24, which is provided with a guide slit 25, through which condylar pin 5, 6 reaches when upper member 9 is placed on lower member 1. Condylar insert 24 is secured in condylar housing 7, 8 in positive and non-positive and/or locking fashion.

In order to guarantee than condylar pin 5, 6 is guided in condylar insert 24 without play, the width of guide slit 25 corresponds roughly to the diameter of condylar pin 5, 6. At least the side of guide slit 25 lying on condylar pin 5, 6 when assembled is designed as a sagittal guideway 28, the path form of which simulates the natural conditions of the human mandibular joint. When viewed in cross-section, sagittal guideway 28 can be of straight, rounded or also prismatic design on either side of guide slit 25. The rounded or prismatic design permits more exact guidance of condylar pin 5, 6 in the guide slit.

In order to be able to fit condylar housing 7, 8 on condylar pin 5, 6, one end of guide slit 25 is open in the direction of lower member 1 of the dental articulator. The corresponding insertion opening 26 can be closed with the aid of a slide 27, so as to prevent unintentional detachment of upper member 9 of the dental articulator.

Furthermore a hook 29, which can be placed over condylar pin 5, 6 in locking fashion, is locked in pivoting fashion on a locating pin 40 projecting from condylar housing 7, 8 in front of its face end 23. To this end, hook 29 is provided with a recess 30, which locks around condylar pin 5, 6 when hook 29 is in place. Recess 30 has the form of an arc with its centre point in the pivot about locating pin 40. This means that upper member 9 can then only be pivoted relative to lower member 1, this facilitating the insertion of the plaster casts, for example, and also permitting simple control of the occlusal overlay in the centric position. Moreover, this also ensures safe transport of the dental articulator. The same function can also be enabled in the protrusion position by means of appropriately designed protrusion clips 29a.

In addition, a spacer ring 31, 32, which can be slid onto condylar pin 5, 6, is also provided, which is slid up against face end 23 of condylar housing 7, 8 and can be fixed there on condylar pin 5, 6 with the aid of a clamping screw 33, 34. This produces locking in the centric position, thus allowing only protrusion and retrusion movements.

Fastening of condylar housing 7, 8 in upper member 9 is achieved in the conventional manner with the aid of a round stud 35, which can be inserted into a corresponding bore in the upper member in positive fashion. As a result, condylar housing 7, 8 can be swung into any desired angular position in order to set the condylar plane.

To permit accurate setting of the angle, condylar housing 7, 8 is provided with a corresponding graduated scale 36, which can be engraved or stuck on, for example.

In order to allow fixing of condylar housing 7, 8 in the desired angular position, a further locking screw 37, 38 is provided which is fitted in upper member 9 and engages a conical taper 39 in stud 35. In this context, taper 39 is designed in such a way that it tapers off towards condylar housing 7, 8, On the one hand, this enables easy adjustment of the angle of condylar housing 7, 8 when locking screw 37, 38 is loosened slightly, meaning that condylar housing 7, 8 cannot be unintentionally pulled off upper member 9 and, on the other hand, condylar housing 7, 8 is drawn up against upper member 9 and thus reliably fixed in place when locking screw 37, 38 is tightened.

Figure 5:
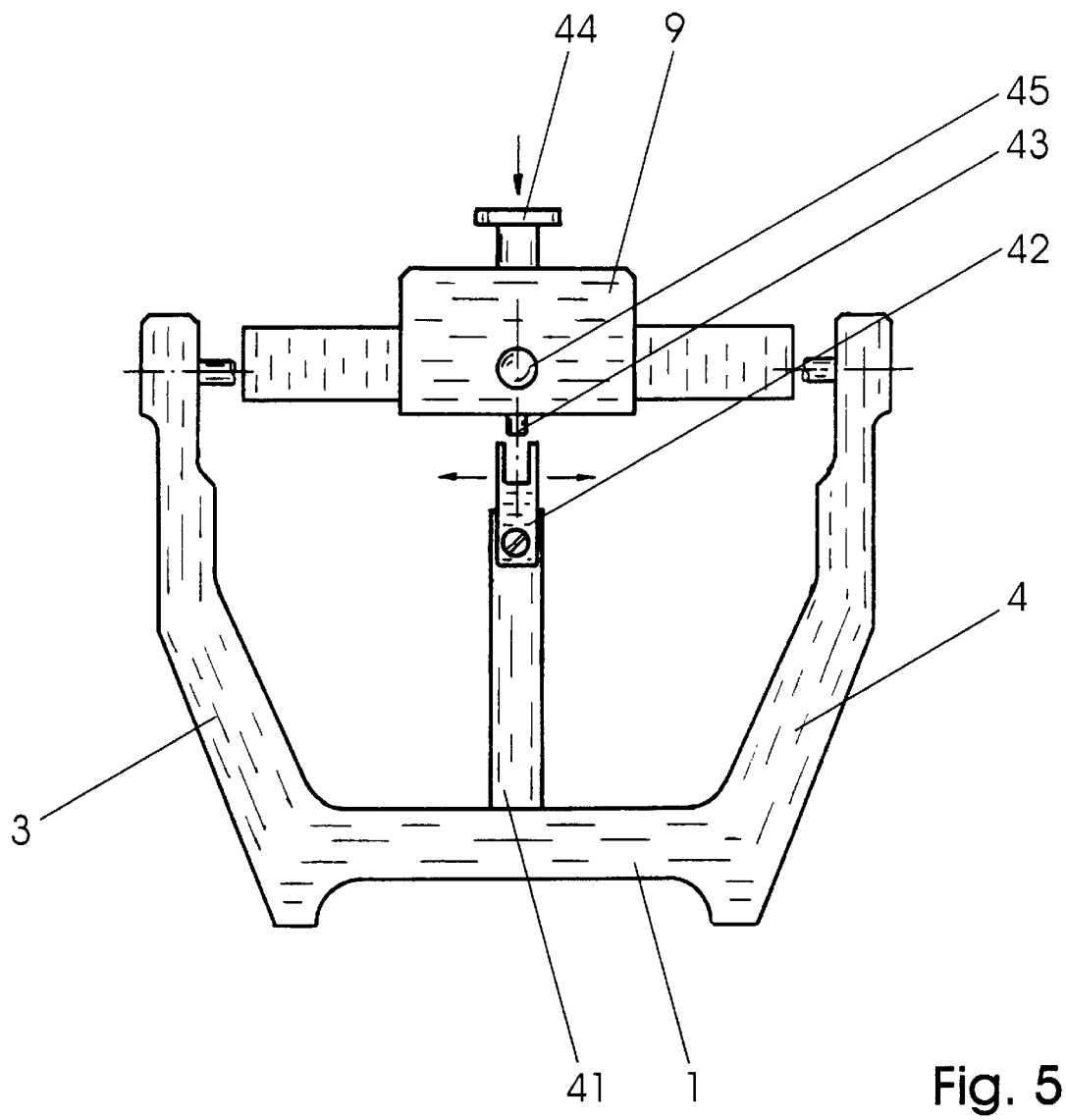
Figure 6:
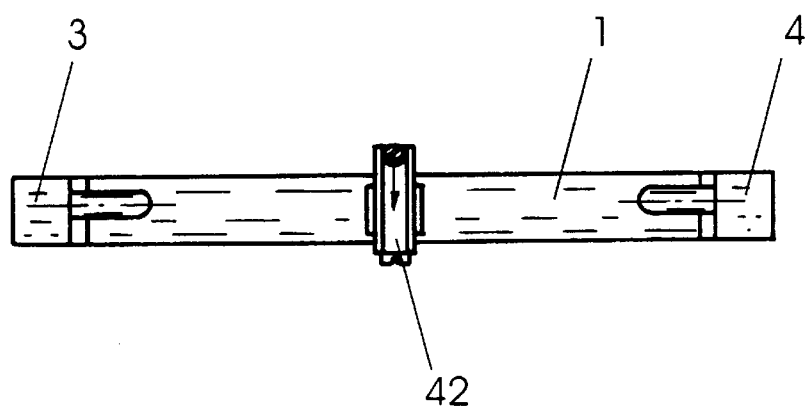

Another version of the centric locking device, not involving the use of spacer rings 31, 32, is illustrated in FIGS. 5 and 6. To this end, an additional post 41 is located between vertical posts 3, 4 on lower member 1, the upper end of which is provided with a centric guide 42. In this context, centric guide 42 can be integrated in additional post 41, or secured on it in adjustable fashion as an additional part.

In this context, centric guide 42 is positioned at such a small distance below upper member 9 that a spring-loaded locking pin 43 in upper member 9 can engage it. To permit easy actuation of locking pin 43, it is provided with a button 44, which protrudes from the middle part of upper member 9.

Furthermore, locking pin 43 can be fixed in locked position by means of a locking screw 45.

Using the centric locking device as per FIGS. 5 and 6, or when using spacer rings 31, 32, an additional retrusion movement is also possible after removing Bennett inserts 18.

Figure 7:
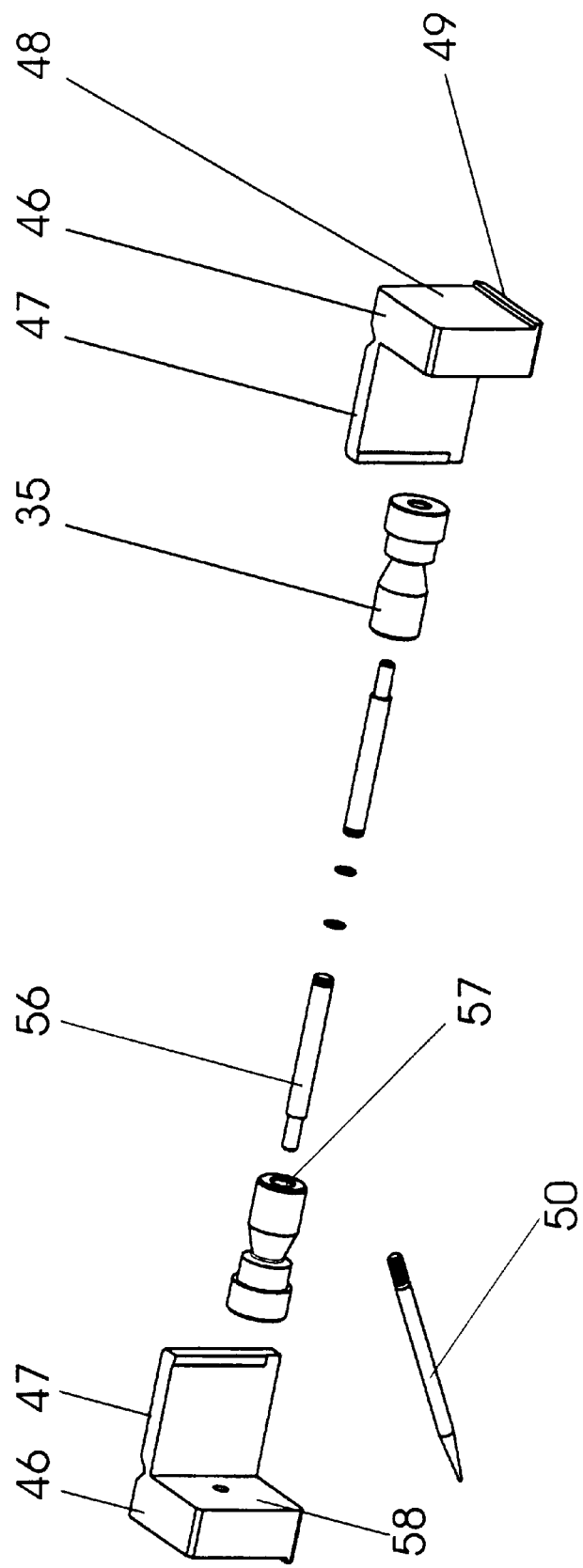
Figure 8:
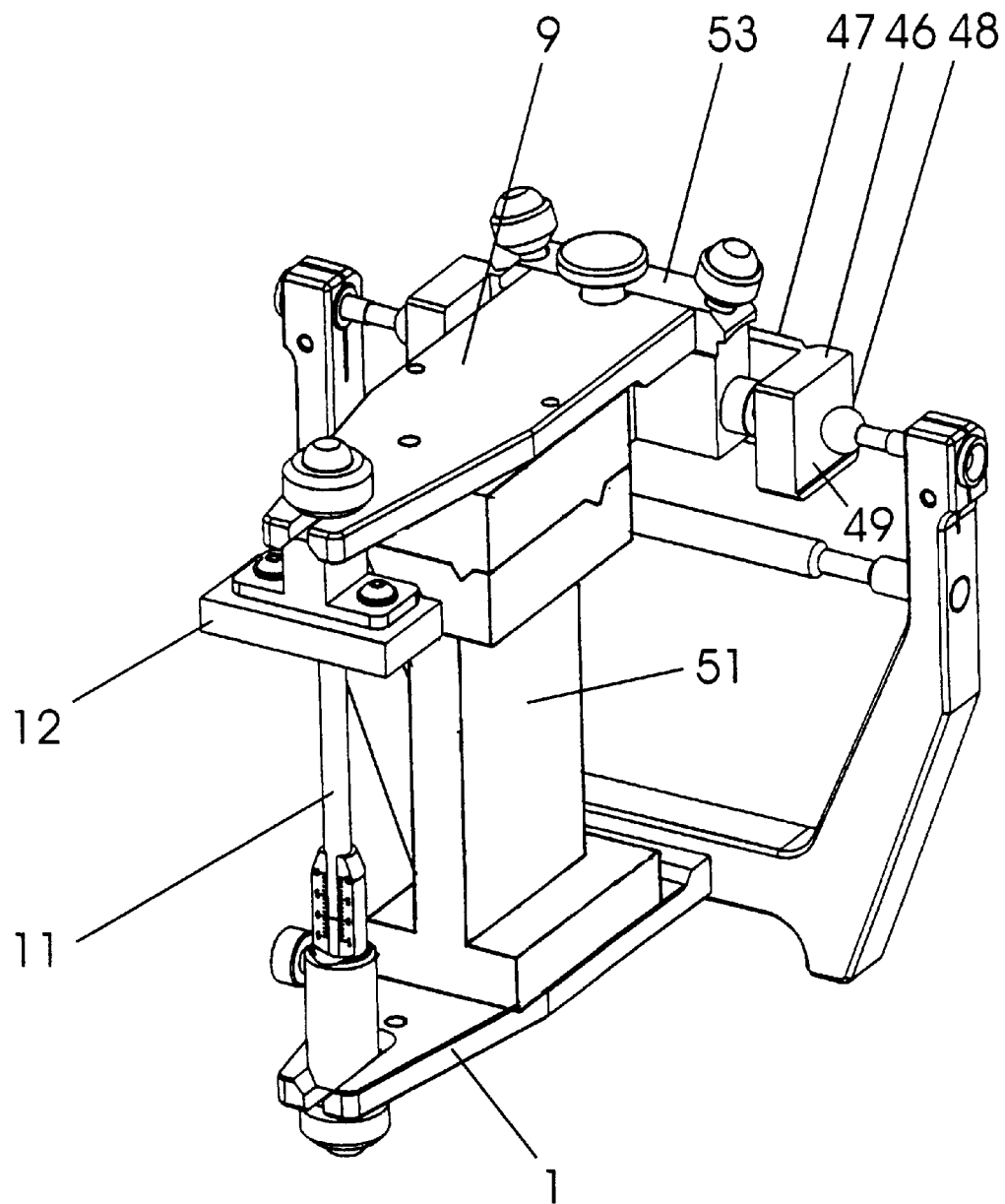

FIG. 7 initially shows the individual components which are necessary for determining the position of the condyles and which must be inserted in upper member 9 of the dental articulator in accordance with FIG. 8 for this purpose. These consist of a measuring cube 46, which is provided with a measuring surface 48 and on which a tab 47, extending inwards in the axial direction, is provided at right angles to measuring surface 48. Measuring surface 48 is used for affixing a label (graph paper) for recording the up/down and backward/forward offset, where a positioning edge 49 is additionally provided in the lower region of measuring surface 48 to permit exact alignment of the label.

Figure 10:
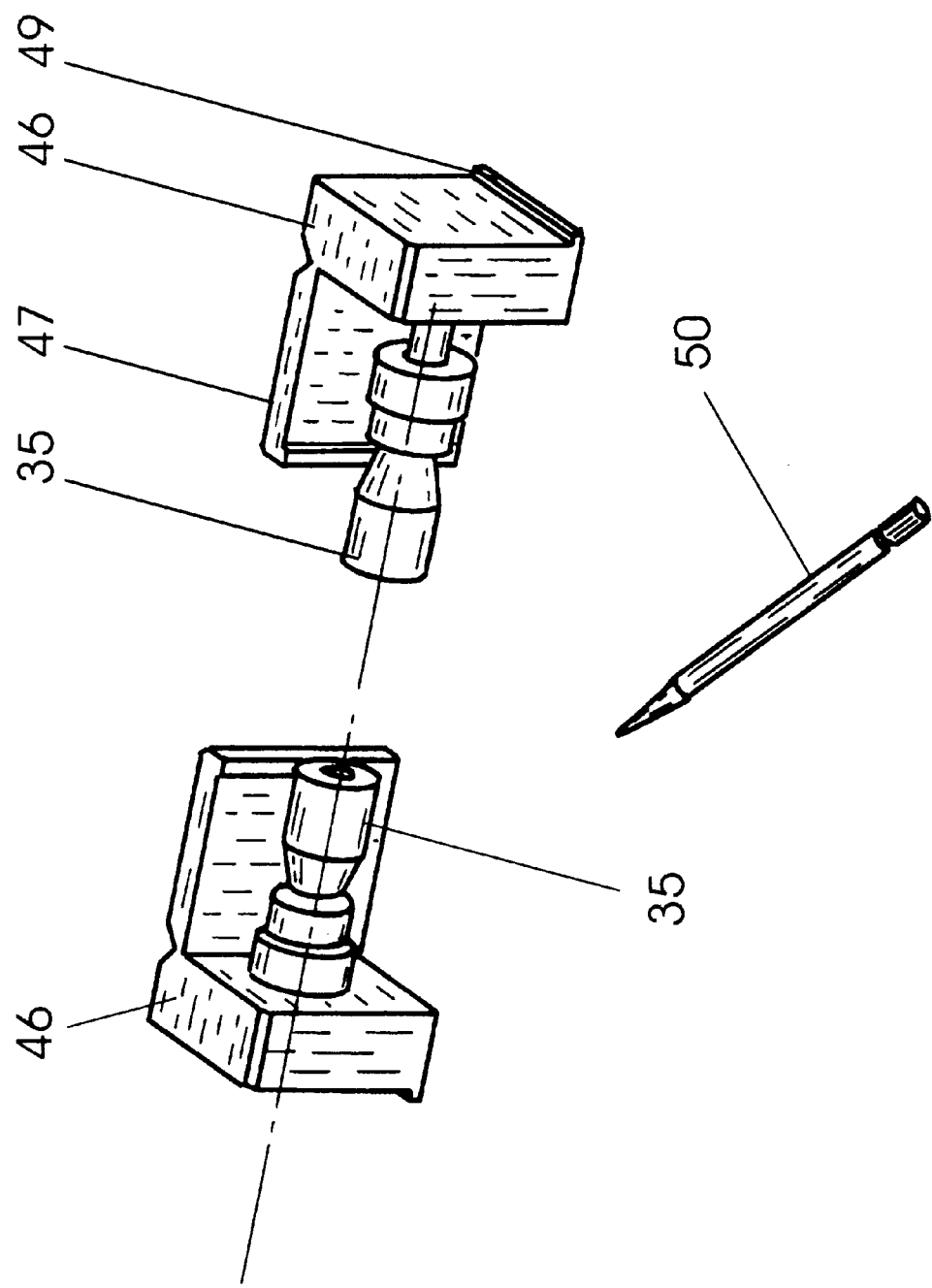

Stud 35 is used for fastening measuring cube 46 on upper member 9 of the dental articulator and has the same shape as stud 35 for fastening condylar housing 7, 8, where the connection between stud 35 and measuring cube 46 is made with the aid of a pin 56, which extends through a bore 57 in stud 35 and into a further bore 58 in measuring cube 46 (FIG. 10). Furthermore, an anti-twist device is provided for measuring cube 46, this being realised simply in that, when measuring cube 46 is inserted, tab 47 lies directly against the rear surface of middle part 53 of upper member 9.

FIG. 8 illustrates a dental articulator where condylar housing 7, 8, which are otherwise present, have been replaced by measuring cubes 46 and where the alignment in space between upper member 9 and lower member 1 is achieved with the aid of a test and adjusting key 51 inserted between the two.

Moreover, a customary incisal pin 11 is inserted between the front ends of upper member 9 and lower member 1, the upper end of which is aligned in such a way that it lies against an incisal guide table 12 fastened on upper member 9.

The position of the condyles can now easily be determined by first replacing the movement-limiting condylar housings 7, 8 of the upper member 9 of the articulator with the non-twisting measuring cubes 46, these being inserted in the axial bores of upper member 9 of the articulator. This eliminates the need to transfer the casts, as the modified upper member 9 of the articulator itself can be used for measuring.

The same test and adjusting key 51 is used for measuring the zero position as is used for fixing the articulator condyles in the zero position. This system of articulator adjustment in known from DE 41 18 138 A1.

Figure 9:
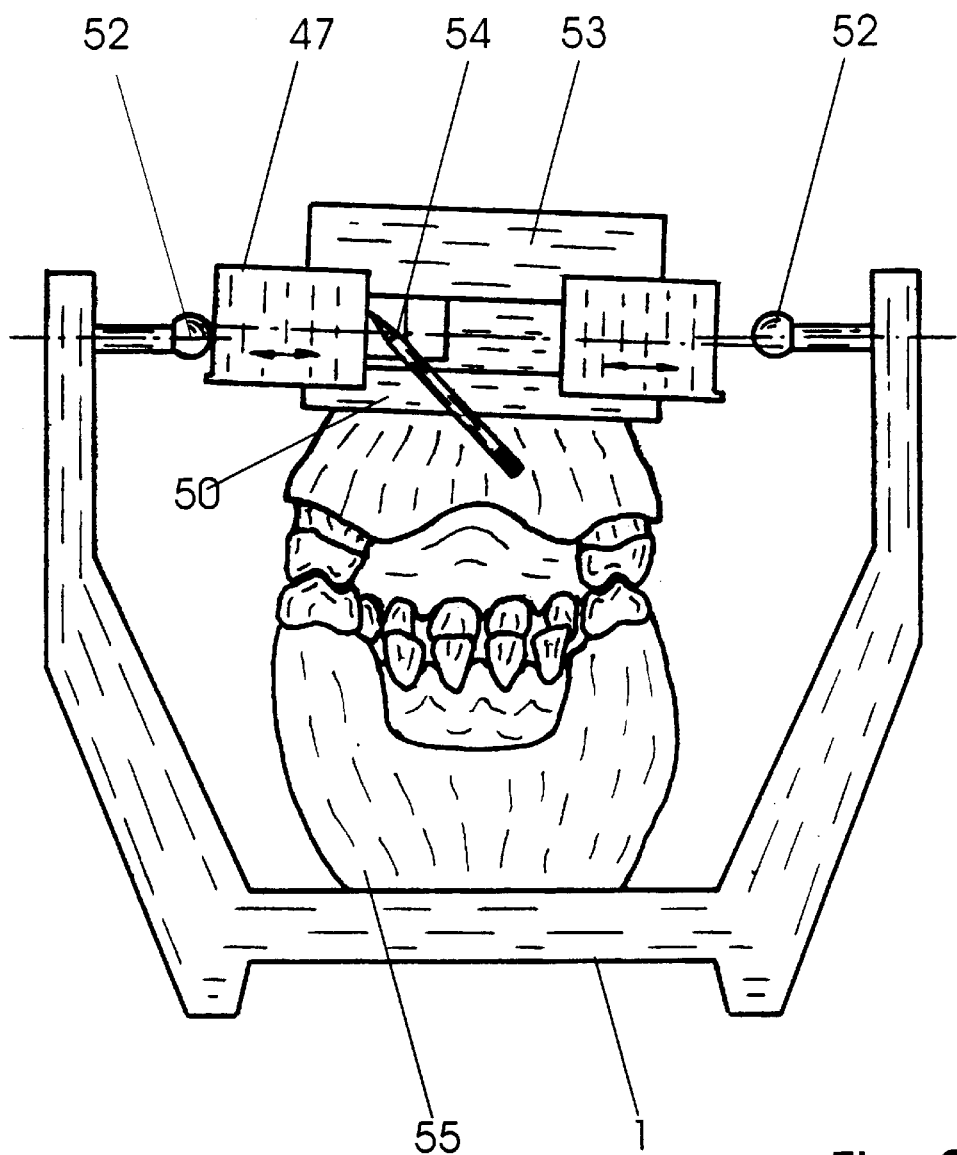

The condyle position is measured with the arrangement according to the invention as follows:

The plaster casts 55 of the upper and lower jaw are first mounted in the corresponding articulator sections 1, 9 and condylar housings 7, 8 of upper member 9 are replaced by measuring cubes 46, whose measuring surfaces 48 are covered with graph paper for recording (FIG. 9). The mounted plaster casts 55 are closed in the position of maximum intercuspitation. After inserting marking film, measuring cubes 46 are moved outwards - the inner sides of the condylar balls on both sides produce a punctual mark on the graph paper, corresponding to the position of the joint axis in the intercuspital position (FIG. 3). A marking indicating the transverse position of the joint axis in space in the intercuspital position can be drawn at tab 47 of the right-hand measuring cube 46 on the rear side of upper member 9 of the articulator using a marker pen 50 on a recording medium 54 previously secured to the rear side of middle part 53.

Plaster casts 55 are then removed and the test and adjusting key 51 is inserted instead. This corresponds to the position of the upper and lower members in zero reference position.

Markings are again made in the manner described above, preferably using a different colour for better distinction.

The labels of measuring cubes 46 can be used to read, measure and document the displacements in the forward/backward and up/down directions on the right and left-hand sides, while recording medium 54 on the rear side of upper member 9 of the articulator is for the lateral displacement of the joint axis between the intercuspital position and the reference position. This measurement can, of course, also be carried out by electronic means.

Dental articulator

List of reference numbers

1 Lower member
2 Mount
3 Vertical post
4 Vertical post
5 Condylar pin
6 Condylar pin
7 Condylar housing
8 Condylar housing
9 Upper member
10 Mount
11 Incisal pin
12 Incisal guide table
13 Opening
14 Locating surface
15 Mount
15' Recess
15" Gap
16 Graduated scale
17 Base surface
18 Bennett insert
19 Slit
20 Locking screw
21 Guide
23 Bennett guide surface
23 Face end
24 Condylar insert
25 Guide slit
26 Insertion opening
27 Slide
28 Sagittal guideway
29 Hook
30 Recess
31 Spacer ring
32 Spacer ring
33 Clamping screw
34 Clamping screw
35 Stub
36 Graduated scale
37 Locking screw
38 Locking screw
39 Taper
40 Locating pin
41 Additional post
42 Centric guide
43 Locking pin
44 Button
45 Locking screw
46 Measuring cube
47 Tab
48 Measuring surface
49 Positioning edge
50 Marker pen
51 Test and adjusting key
52 Condyle
53 Middle part
54 Recording medium
55 Plaster cast
56 Pin
57 Bore
58 Bore

We claim:

1. Dental articulator having upper and lower members (9, 1), with condylar housings located on the upper member for accommodating and guiding condyles fixed to the lower member, where guide elements for the condyles for simulating the sagittal movements of the mandibular joint and Bennett guide elements for simulating the transverse movements of the mandibular joint are located in the condylar housing, characterised in that, for spatially controlled guidance on a laterotrusion side, each condyle comprises a condylar pin (5, 6) which extends along a joint axis through a condylar guide in the condylar housing (7, 8) connected to the upper member (9) of the articulator in detachable fashion through a guide slit (25) in a condylar insert (24) into the condylar housing (7, 8), in that a free end of the condylar pin (5, 6) can be positioned against a guide surface (22) of a Bennett guide element, which comprises a variable-angle Bennett insert (18), in the condylar housing (7, 8), in that directions of action of a sagittal guideway (28) of the condylar insert (24) for condylar guidance and of the guide surface (22) of the Bennett insert (18) are perpendicular to each other, and in that the condylar housing (7, 8) is open on one side in the direction of the upper side of the dental articulator.

2. Dental articulator according to claim 1, characterised in that the condylar housing (7, 8) is provided with an arc-shaped locating surface (14) opposite the condylar insert (24) to accommodate and allow limited swivelling of a mount (15) with a semi-circular cross-section for the Bennett insert (18).

3. Dental articulator according to claim 2, characterised in that the mount (15) can be fixed on position at a given angle on the locating surface (14).

4. Dental articulator according to claim 3, characterised in that the mount (15) has a locking screw (20) which reaches through an arc-shaped slit (19) in a base surface (17) of the condylar housing (7, 8), and in that the mount (15) can be fixed on the base surface (17) by means of the locking screw (20).

5. Dental articulator according to claim 4, characterised in that the mount (15) has a guide (21), into which the Bennett insert (18) can be inserted in positive and slightly non-positive fashion through an opening (13) in the condylar housing (7, 8).

6. Dental articulator according to claim 5, characterised in that one side of the guide (21) has a recess (15') and a small gap (15") is left free between the locating surface (14) and an outer surface of the mount (15) opposite the recess (15') up to an end of the outer surface of the mount (15).

7. Dental articulator according to claim 1, characterised in that the condylar insert (24) is fastened in the condylar housing (7, 8) in replaceable fashion and has a guide slit (25), one end of which is open in a direction of the lower member (1) of the dental articulator.

8. Dental articulator according to claim 7, characterised in that a width of the guide slit (25) roughly corresponds to a diameter of the condylar pin (5, 6).

9. Dental articulator according to claim 1 or 7, characterised in that the condylar insert (24) can be fastened in the condylar housing (7, 8) positively and non-positively and/or in locking fashion.

10. Dental articulator according to claim 1, characterised in that at least a side of the slit (19) lying on the condylar pin (5, 6) in working condition is designed in accordance with natural condylar guidance.

11. Dental articulator according to claim 1, characterised in that an angle of the condylar housing (7, 8) is adjustable about the joint axis.

12. Dental articulator according to claim 1, characterised in that each side of the upper member (9) of the dental articulator is provided with a condylar housing (7, 8), where a condylar pin (5, 6) projecting inwards from the vertical post (3, 4) of the dental articulator protrudes into each condylar housing (7, 8).

13. Dental articulator according to claim 12, characterised in that degrees of freedom of the condylar pin (5, 6) in the condylar housing (7, 8) can be restricted.

14. Dental articulator according to claim 13, characterised in that the condylar housing (7, 8) has an articulated hook (29) which can be swung onto the condylar pin (5, 6) in front of the condylar insert (24) and which fixes a condylar joint in a centric position on the condylar pin (5, 6).

15. Dental articulator according to claim 14, characterised in that the hook (29) can be positioned on the condylar pin (5, 6) in locking fashion.

16. Dental articulator according to claim 13, characterised in that the condylar pin (5, 6) has an axially movable spacer ring (31, 32) which can be fixed on the condylar housing (7, 8).

17. Dental articulator according to claim 13, characterised in that an additional post (41) is located between vertical posts (3, 4) on the lower member (1), the upper end of the lower member 1 having an adjustable centric guide (42) into which a locking pin (43) mounted on the upper member (9) can be inserted.

18. Dental articulator according to claim 1, characterised in that a free end of the condylar pin (5, 6) is rounded in the manner of a spherical cap or ends in a ball or an undercut ball or a spherical cap.

19. Dental articulator having a upper and lower members (9, 1) with condylar housings located in interchangeable fashion in mounts on the upper member of the dental articulator for accommodating and guiding conyles fixed to the lower member, characterised in that a measuring cube (46) movable along a hinge axis is inserted in each mount, in that each measuring cube (46) has an anti-twist device and has a measuring surface (48) opposite the associated condyles (52) which measuring surface (48) is used for affixing a label for indicating up/down and backward/forward offset, in that the measuring surface (48) with the affixed label can be pressed against the condyle (52) at a contact point and in that the measuring cube (46) is provided with a stud (35) for inserting into the mount of the upper member (9) and has a tab (47) which extends inwards in an axial direction and can be adjustably positioned flat against a rear surface of the upper member (9).

20. Arrangement according to claim 19, characterised in that the measuring surface (48) has a positioning edge (49) for the label.

21. Arrangement according to claim 20, characterised in that the measuring cubes (46) with the measuring surfaces (48) can be moved against the condyles (52) after inserting a marking film.

22. Arrangement according to claim 21, characterised in that the measuring cubes (46) can be moved independently of each other.

23. Arrangement according to claim 22, characterised in that the rear surface of the upper member (9) has recording medium (54) below the tab (47) for recording a transverse offset with a marker pen (50).

* * * * *